(12) United States Patent
Hanna

(10) Patent No.: US 12,073,736 B2
(45) Date of Patent: Aug. 27, 2024

(54) TECHNOLOGIES FOR WOUND TREATMENT EDUCATION

(71) Applicant: Phokus Research Group, LLC, Rye, NY (US)

(72) Inventor: Robert J. Hanna, San Diego, CA (US)

(73) Assignee: Phokus Research Group, LLC, Rye, NY (US)

( * ) Notice: Subject to any disclaimer, the term of this patent is extended or adjusted under 35 U.S.C. 154(b) by 999 days.

(21) Appl. No.: 16/758,563

(22) PCT Filed: Oct. 24, 2018

(86) PCT No.: PCT/US2018/057343
§ 371 (c)(1),
(2) Date: Apr. 23, 2020

(87) PCT Pub. No.: WO2019/084160
PCT Pub. Date: May 2, 2019

(65) Prior Publication Data
US 2020/0349864 A1  Nov. 5, 2020

Related U.S. Application Data

(60) Provisional application No. 62/576,596, filed on Oct. 24, 2017.

(51) Int. Cl.
*G09B 23/30* (2006.01)
*A61M 1/00* (2006.01)

(52) U.S. Cl.
CPC ............. *G09B 23/303* (2013.01); *A61M 1/90* (2021.05)

(58) Field of Classification Search
CPC ....... G09B 23/28; G09B 23/30; G09B 23/303
See application file for complete search history.

(56) References Cited

U.S. PATENT DOCUMENTS

| | | | | |
|---|---|---|---|---|
| 3,027,655 A | * | 4/1962 | Alderson | G09B 23/32 434/268 |
| 3,426,449 A | † | 2/1969 | Van Noy, Jr. | |
| 3,704,529 A | * | 12/1972 | Cioppa | G09B 23/285 128/207.29 |
| 3,852,893 A | * | 12/1974 | Smrcka | G09B 23/32 264/DIG. 14 |
| 4,198,766 A | * | 4/1980 | Camin | G09B 23/285 434/272 |

(Continued)

FOREIGN PATENT DOCUMENTS

| | | |
|---|---|---|
| CN | 104641407 A | 5/2015 |
| DE | 102011112795 A1 | 3/2013 |

OTHER PUBLICATIONS

Calderone, This video demonstrates how incredibly damaging bullet wounds can be, Business Insider Jan. 2016, http://www.businessinsider.in/This-video-demonstrates-how-incredibly-damaging-bullet-wounds-can-be/articleshow/50549781.cms (2 pages).

(Continued)

*Primary Examiner* — Kurt Fernstrom
(74) *Attorney, Agent, or Firm* — Dentons US LLP

(57) ABSTRACT

A method comprising: accessing a block that is not opaque and defines a plurality of wells that are not in fluid communication with each other; and providing a storage medium storing a set of instructions on how to use the block.

42 Claims, 10 Drawing Sheets

(56) References Cited

U.S. PATENT DOCUMENTS

| | | | | |
|---|---|---|---|---|
| 5,055,051 A * | 10/1991 | Duncan | | A61B 8/587 |
| | | | | 434/262 |
| 5,775,916 A * | 7/1998 | Cooper | | G09B 23/28 |
| | | | | 434/272 |
| 6,241,525 B1 * | 6/2001 | Spitalnik | | G09B 23/28 |
| | | | | 434/262 |
| 7,427,199 B2 * | 9/2008 | Sakezles | | G09B 23/28 |
| | | | | 434/267 |
| 7,850,454 B2 | 12/2010 | Toly | | |
| 7,887,330 B2 * | 2/2011 | King | | G09B 23/303 |
| | | | | 434/268 |
| 8,221,129 B2 * | 7/2012 | Parry | | G09B 9/003 |
| | | | | 434/274 |
| 8,535,062 B2 * | 9/2013 | Nguyen | | G09B 23/30 |
| | | | | 434/267 |
| 8,568,147 B2 * | 10/2013 | Kuo | | G09B 23/30 |
| | | | | 434/262 |
| 8,647,124 B2 | 2/2014 | Bardsley et al. | | |
| 8,672,684 B2 | 3/2014 | Ray | | |
| 8,827,720 B1 | 9/2014 | Lazarus et al. | | |
| 8,911,238 B2 * | 12/2014 | Forsythe | | G09B 23/28 |
| | | | | 434/267 |
| 9,240,130 B2 | 1/2016 | Carvajal et al. | | |
| 9,607,528 B2 | 3/2017 | Meglan et al. | | |
| 9,916,774 B2 * | 3/2018 | Segall | | G09B 23/28 |
| 10,803,761 B2 * | 10/2020 | Welch | | G06T 19/006 |
| 10,885,813 B2 * | 1/2021 | Krummenacher | | G09B 23/30 |
| 11,158,212 B2 * | 10/2021 | Hoke | | G09B 23/28 |
| 11,238,756 B2 * | 2/2022 | Carroll | | G09B 23/303 |
| 11,600,200 B2 * | 3/2023 | Hare | | G09B 23/303 |
| 11,955,030 B2 * | 4/2024 | Taylor | | G09B 23/303 |
| 2003/0073060 A1 | 4/2003 | Eggert et al. | | |
| 2004/0117035 A1 | 6/2004 | Williams et al. | | |
| 2004/0180314 A1 * | 9/2004 | Charbonneau | | G09B 23/28 |
| | | | | 434/273 |
| 2005/0186361 A1 * | 8/2005 | Fukuda | | G09B 23/30 |
| | | | | 264/497 |
| 2009/0011394 A1 | 1/2009 | Meglan et al. | | |
| 2009/0017431 A1 * | 1/2009 | Adams | | G09B 23/288 |
| | | | | 434/265 |
| 2010/0160894 A1 * | 6/2010 | Julian | | A61P 19/02 |
| | | | | 434/262 |
| 2012/0045742 A1 * | 2/2012 | Meglan | | G09B 23/303 |
| | | | | 434/268 |
| 2014/0011172 A1 | 1/2014 | Lowe | | |
| 2014/0051050 A1 | 2/2014 | Fradette et al. | | |
| 2016/0171911 A1 | 6/2016 | Parry, Jr. et al. | | |
| 2016/0247419 A1 * | 8/2016 | Parry | | G09B 9/003 |
| 2019/0088163 A1 * | 3/2019 | Jabbour | | G09B 9/00 |
| 2020/0170649 A1 * | 6/2020 | Hallbeck | | A61B 5/6828 |

OTHER PUBLICATIONS

International Search Report and Written Opinion dated Jan. 17, 2019 in related International Application PCT/US18/57343 filed Oct. 24, 2018 (10 pages).

\* cited by examiner
† cited by third party

TECHNOLOGIES FOR WOUND TREATMENT EDUCATION

CROSS REFERENCE TO RELATED APPLICATIONS

The present application claims the benefit of PCT International Application No. PCT/US18/57343 filed 24 Oct. 2018; which claims the benefit of U.S. Provisional Application Ser. No. 62/576,596 filed 24 Oct. 2017; which is incorporated herein by reference in its entirety.

TECHNICAL FIELD

This disclosure relates to wound treatment education.

BACKGROUND

Since wounds, whether gunshot, knife, shrapnel, or others, are fairly graphical, many law enforcement, military, and medical personnel train on mannequins or other simulators in order to desensitize the personnel and to prevent mental shock when exposed to the wounds during deployment. However, even such simulators have various drawbacks, such as an inability to observe whether and how various treatments are working internally or how various internal musculature, bones, organs, or body fluid vessels are affected by the treatments or how to simulate various bleeding wounds of various intensities in various body areas. Further, during training, many trainees don't know how to find the source of bleeding, clear blood from the cavity, and then pack wounds with a gauze strip, while applying adequate wound pressure. Therefore, there is a desire for a technology to address such drawbacks.

SUMMARY

An embodiment includes a method comprising: accessing a block that is not opaque and defines a plurality of cavities that are not in fluid communication with each other; and providing a storage medium that stores a set of instructions on how to use the block.

In another embodiment, the wells are different from each other in shape or in volume.

In another embodiment, the block is at least one of transparent or translucent.

In another embodiment, the block includes a side from which the wells extend, or the block includes a plurality of sides from which the wells extend, wherein the sides correspond to the wells in a one-to-one manner.

In another embodiment, the block is at least one of polygonal, a sphere, an ovoid, or an ellipsoid.

In another embodiment, at least one of the wells includes an inner surface that is at least one of smooth or rough.

In another embodiment, the block includes at least one of a gelatin or a silicon.

In yet another embodiment, the block contains a simulator of at least one of a bone or a vessel of a bodily fluid.

In another embodiment, the method further comprises inserting a gauze strip into at least one of the wells.

In another embodiment, the method further comprises outputting a fluid from the block.

In another embodiment, the fluid simulates a blood.

In another embodiment, the block includes a pressure sensor configured to output a signal based on a force applied thereto. In certain embodiments, the pressure sensor is internal to at least one of the wells.

In another embodiment, the opacity of the block changes based on upon application of at least one of a chemical, an electrical signal, or a light source.

One embodiment, includes a device comprising: a block that is not opaque and that defines a plurality of wells that are not in fluid communication with each other, wherein the block contains at least one of a simulator of a bone or a vessel of a bodily fluid.

This disclosure is embodied in various forms illustrated in a set of accompanying illustrative drawings. Note that variations are contemplated as being a part of this disclosure, limited only by a scope of various claims recited below.

BRIEF DESCRIPTION OF DRAWINGS

The set of accompanying illustrative drawings shows various example embodiments of this disclosure. Such drawings are not to be construed as necessarily limiting this disclosure. Like numbers and/or similar numbering scheme can refer to like and/or similar elements throughout.

DETAILED DESCRIPTION

Figure 1:
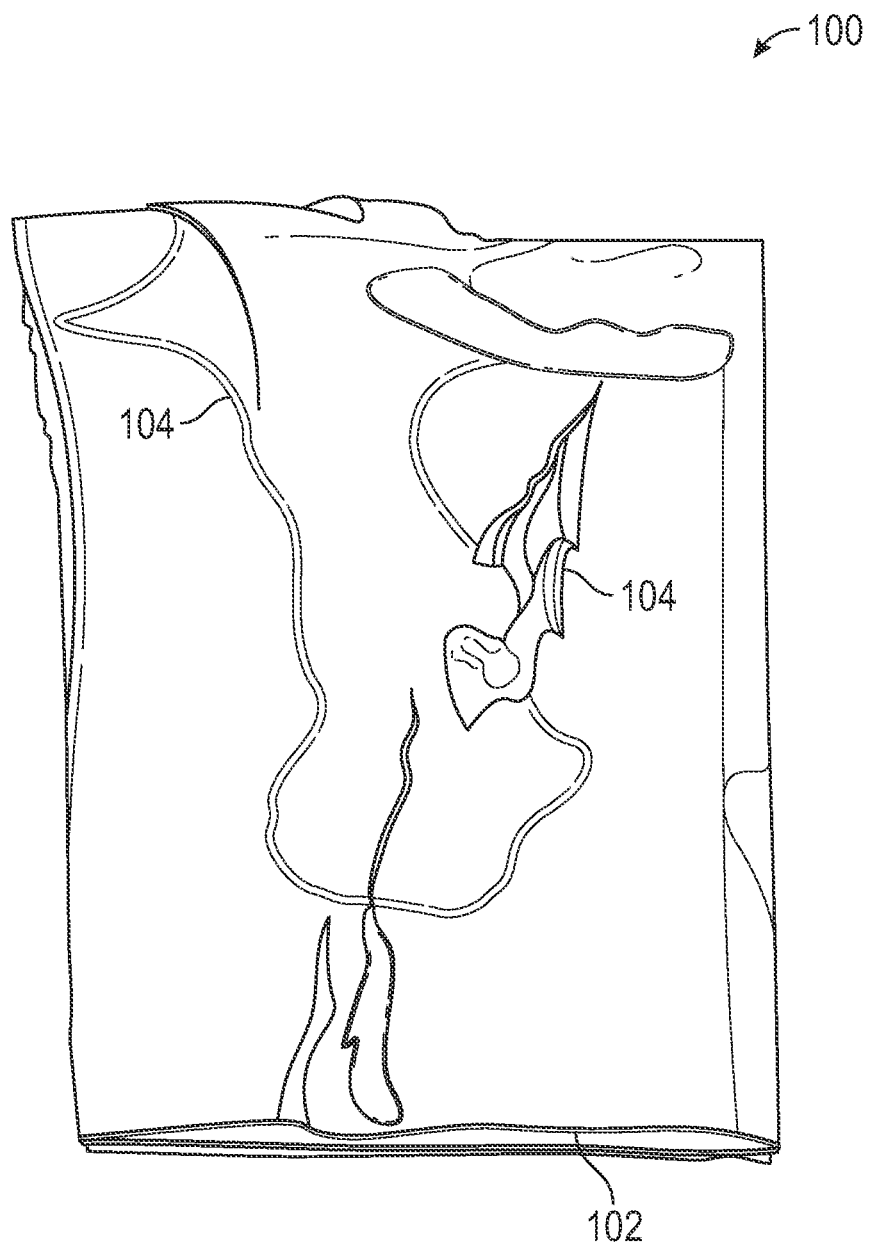
FIG. 1 depicts a diagram of an embodiment of a block from a first perspective, according to this disclosure.

Generally, this disclosure discloses a block that is not opaque and that defines a plurality of wells that are not in fluid communication with each other. Alternatively, at least some of the wells may be in fluid communication with each other. In some embodiments, the block may be opaque or semi-transparent. In some embodiments, the block or material in which the wells are positioned may comprise a photosensitive material that darkens in appearance upon exposure to light and lightens in appearance upon removal of light. Alternatively, the block or material in which the wells are positioned may comprise a photosensitive material that may lighten in appearance upon exposure to light and darken in appearance upon removal of light.

Alternatively, in some embodiments, the block or material in which the wells are positioned may comprise a electro-sensitive material that darkens in appearance upon exposure to an electric field, magnetic field, current or voltage and lightens in appearance upon removal of electric field, magnetic field, voltage or current. Alternatively, the block or material in which the wells are positioned may comprise an electro-sensitive material that may lighten in appearance upon exposure to an electric field, magnetic field, current or voltage and darken in appearance upon removal of the electric field, magnetic field, current or voltage.

Alternatively, in some embodiments, the block or material in which the wells are positioned may comprise a chemical-sensitive material that darkens in appearance upon exposure to or application of a specific chemical and lightens in appearance upon removal of the chemical or exposure to or application of a different chemical. Alternatively, the block or material in which the wells are positioned may comprise a chemical-sensitive material that may lighten in appearance upon exposure to or application of a specific chemical and darken in appearance upon removal of the chemical or exposure to or application of a different chemical.

The block can be used to educate a user on how to treat a wound, whether entry or exit, such as a gun wound, a knife wound, a shrapnel wound, a puncture wound, or others, with the wound being represented by at least one of the wells. In some embodiments, the plurality of wells may be embodied in the form of a cylinder. In some further embodiments, the plurality of wells may be embodied in the form of a sleeve, hollow cylinder or hollow rectangular or other shaped block, such that it can be secured to or slid onto a subject, such as, for example, to an arm or a leg, or a portion of a skeleton (simulated or real) for simulation of a real wound. However, this disclosure is now described more fully with reference to the set of accompanying illustrative drawings, in which example embodiments of this disclosure are shown. This disclosure can be embodied in many different forms and should not be construed as necessarily being limited to the example embodiments disclosed herein. Rather, the example embodiments are provided so that this disclosure is thorough and complete, and fully conveys various concepts of this disclosure to those skilled in a relevant art.

Various terminology used herein can imply direct or indirect, full or partial, temporary or permanent, action or inaction. For example, when an element is referred to as being "on," "connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

Although terms first, second, and others can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from various teachings of this disclosure.

Various terminology used herein is for describing particular example embodiments and is not intended to be necessarily limiting of this disclosure. As used herein, various singular forms "a," "an" and "the" are intended to include various plural forms as well, unless a context clearly indicates otherwise. Various terms "comprises," "includes" and/ or "comprising," "including" when used in this specification, specify a presence of stated features, integers, steps, operations, elements, and/or components, but do not preclude the presence and/or addition of one or more other features, integers, steps, operations, elements, components, and/or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

Figure 2:
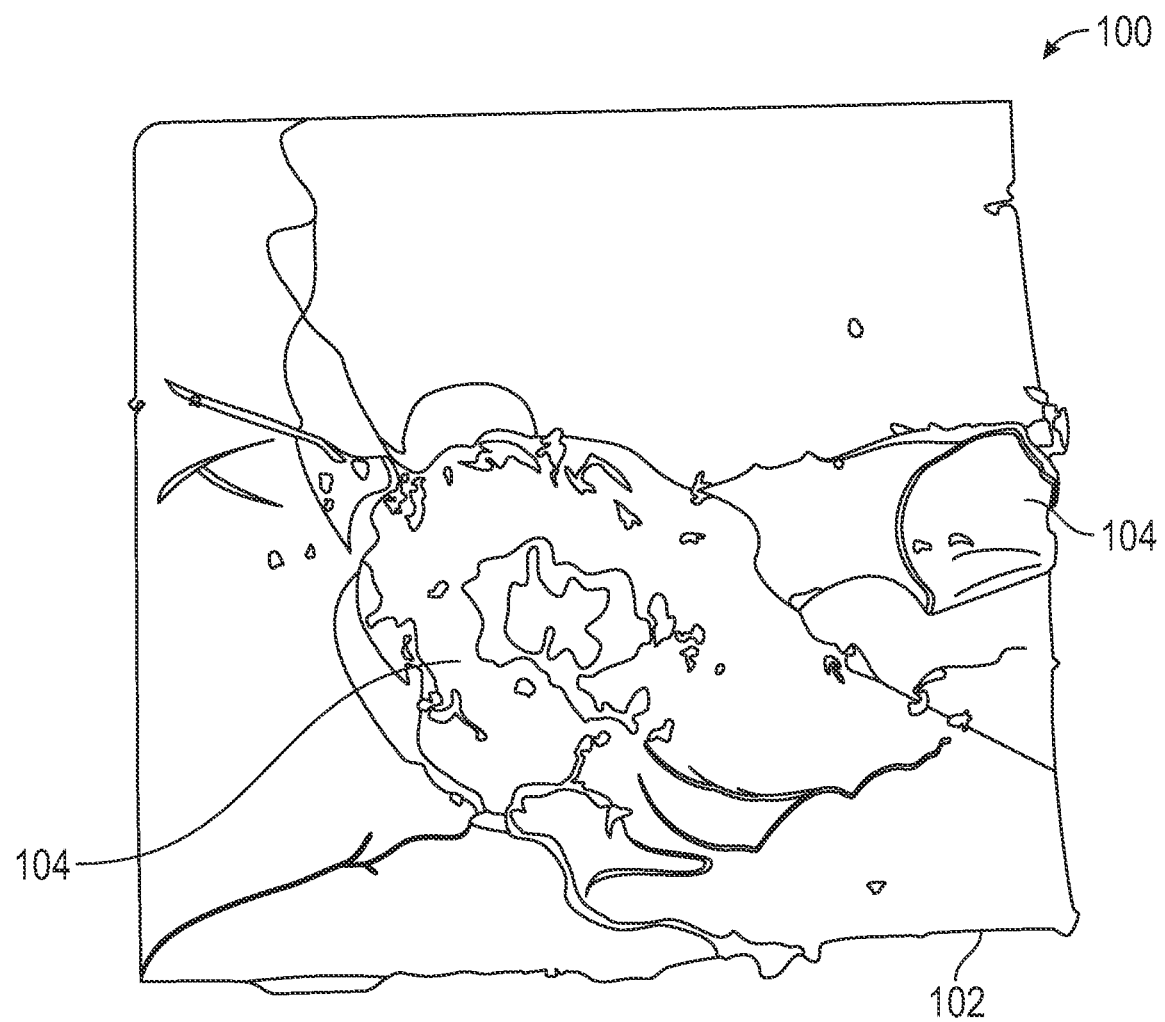
FIG. 2 depicts a diagram of an embodiment of a block from a second perspective, according to this disclosure.
Figure 3:
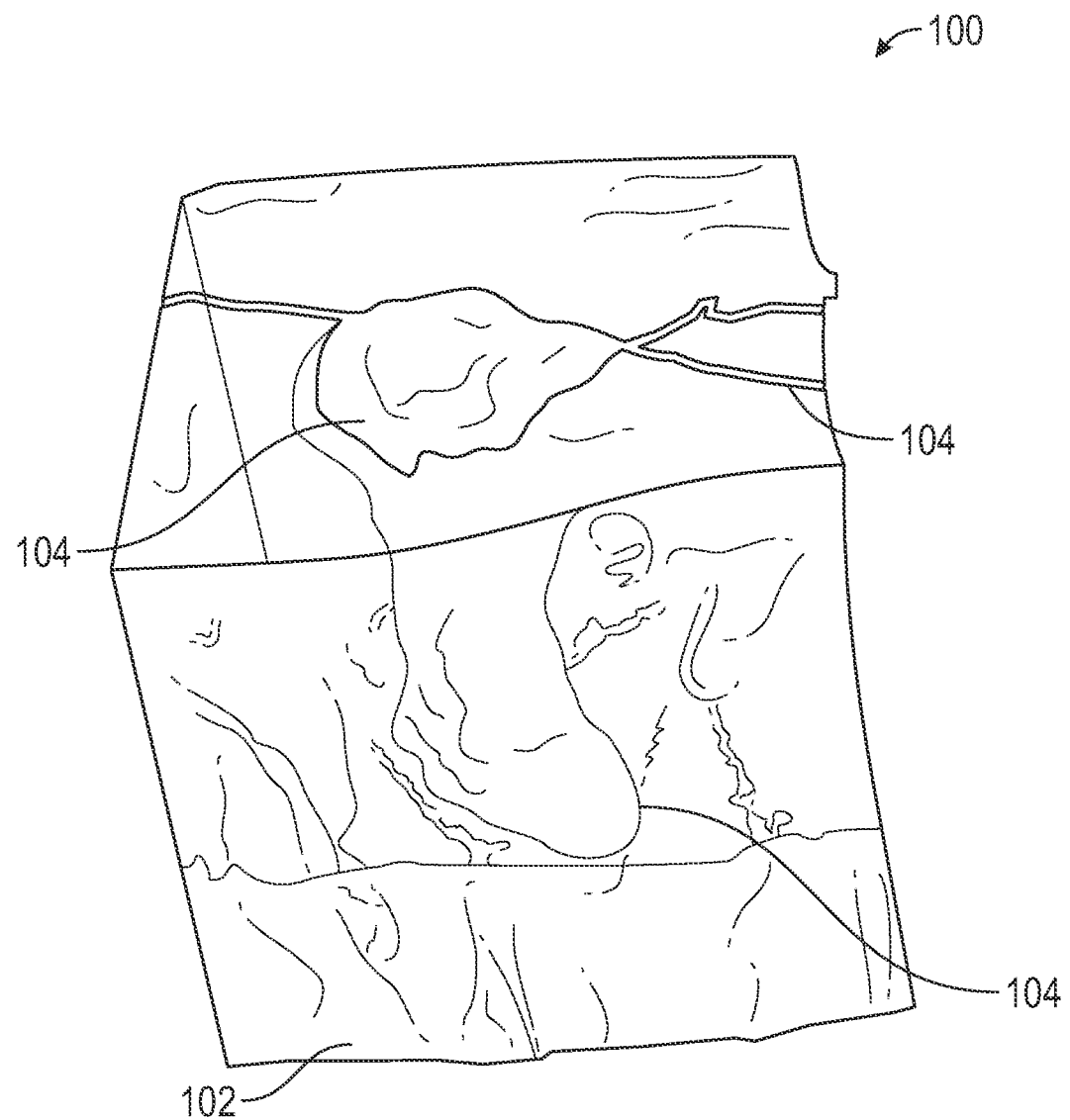
FIG. 3 depicts a diagram of an embodiment of a block from a third perspective, according to this disclosure.

FIGS. 1-3 depict a diagram of an embodiment of a block according to this disclosure. In particular, a block 100 contains a body 102 and a plurality of wells 104 defined therein. The body 102 is not opaque, such as via being transparent or translucent. For example, the body 102 includes at least one of a gelatin or a silicon or another suitable material, such as a rubber, a plastic, or others. For example, the body 102 can include a clear gelatin or a clear silicon. In some embodiments, the body 102 can include a colored gelatin or colored silicon. The body 102 is cube-shaped, but other shapes are possible, such as a cuboid, a pyramid, a wedge, a sphere, an ovoid, an ellipsoid, or any other polygonal or non-polygonal shape. In some embodiments, when the body 102 is cube-shaped, then the body 102 can be sized as 1×1×1 inches, 2×2×2 inches, 3×3×3 inches, 4×4×4 inches, 5×5×5 inches, 6×6×6 inches, or more than 6×6×6 inches or 7×7×7 cm, 8×8×8 cm, 9×9×9 cm, 10×10× 10 cm, 11×11×11 cm, 12×12×12 cm, 13×13×13 cm, 14×14× 14 cm, 15×15×15 cm, or more than 15×15×15 cm. In some embodiments, the body can be sized as 4×4×8 cm, 5×5×10 cm, 6×6×12 cm, 7×7×14 cm, 8×8×16 cm, 9×9×18 cm, 10×10×20 cm, 11×11×22 cm, 12×12×24 cm, 13×13×26 cm, 14×14×28 cm, 15×15×30 cm, or more than 15×15×30 cm. In some embodiments, the body 102 may be opaque or semi-transparent.

The wells 104 are not in fluid communication with each other and can be identical or non-identical to each other in size, shape, volume, inner surface texture, or others. The wells 104 extend from different sides of the body 102, although a single side of the body 102 can host at least two of the wells 104. The wells 104 can be shaped in any way, such as conical, rectilinear, sinusoidal, pyramidal, wedge, tapered, ovoid, or others. The wells 104 include inner surfaces, which may be smooth or rough in texture. In some embodiments, at least one of the wells 104 is not a well but a channel extending across the body 102 end to end and in fluid communication with ambient air on both end portions. In some embodiments, two or more of the wells 104 are in fluid communication with each other.

In certain embodiments, the body 102 contains a simulator of a bone, such as a dye, a strip, a shaft, a bar, a bone, a graft, an artifact, or others. In certain embodiments, for example, the simulator includes at least one of plastic, metal, rubber, wood, bone, or other materials. Note that the simulator is visible within the body 102. As such, the simulator is visually distinct from the body 102, such as via contrast, color, or others. The bone can be any bone within a mammal, such as a human or others. For example, the bone can include a rib, a femur, a collarbone, ulna, radian, tibia, hip, spine, or any other bone. Note that the bone can include a joint, such as a ball and socket joint or others. In some embodiments, the simulator is not visible or only partially visible within the body 102.

In certain embodiments, the body 102 contains a simulator of a vessel of a bodily fluid, such as via a tube, a conduit, a channel, or others. In certain embodiments, for example, the simulator includes at least one of plastic, metal, rubber, wood, or other materials. Note that the simulator is visible within the body 102. As such, the simulator is visually distinct from the body 102, such as via contrast, color, or others. In some embodiments, the vessel is not visible or only partially visible within the body 102. In certain embodiments, the vessel is any vessel within a mammal, such as a human or others. In certain embodiments, for example, the vessel includes an artery, a vein, a trachea, a windpipe, or others. Note that in certain embodiments, the vessel includes an intersection of vessels. In certain embodiments, the bodily fluid includes blood, saliva, urine, or others. As such, in certain embodiments, the fluid is simulated based on color, consistency, texture, or others. For example, in certain embodiments, the fluid is red in color to simulate blood or thick to simulate mucus. Therefore, in certain embodiments, the fluid is output via the simulator from the body 102. In some embodiments, a source of the fluid is contained within the body 102 or external to the body 102. In certain embodiments, the source of the fluid includes a reservoir and a pump, with the reservoir containing the fluid and the pump pumping the fluid. In some embodiments, at least one of the body 102 or at least one of the wells 104 includes a pressure sensor, whether analog or digital, configured to sense if the user is applying appropriate wound pressure and outputs a signal based on the sensing, such as to a bulb or a speaker, if the appropriate wound pressure passes or fails to pass a predefined threshold. In some embodiments, the signal from the pressure sensor is used to control the pump, such as, for example, activating or deactivating the pump. In some embodiments, at least one of the wells 104 is configured to receive a gauze strip. Therefore, the gauze strip can be manually inserted into that well 104 to stop the simulator of the vessel of the bodily fluid from outputting the bodily fluid, such as to educate on how to stop or stem bleeding or others.

In certain embodiments, the block 100 is used as a kit that comes with a storage medium storing a set of instructions on how to use the block 100. In certain embodiments, for example, the storage medium includes a pamphlet, a guide, textbook, a text/email/social message, an app, a webpage, or others. In certain embodiments, for example, the set of instructions includes a text, an image, a video, a sound, a haptic, a vibration, an app, a circuit or processor executable instruction, or others.

Figure 4:
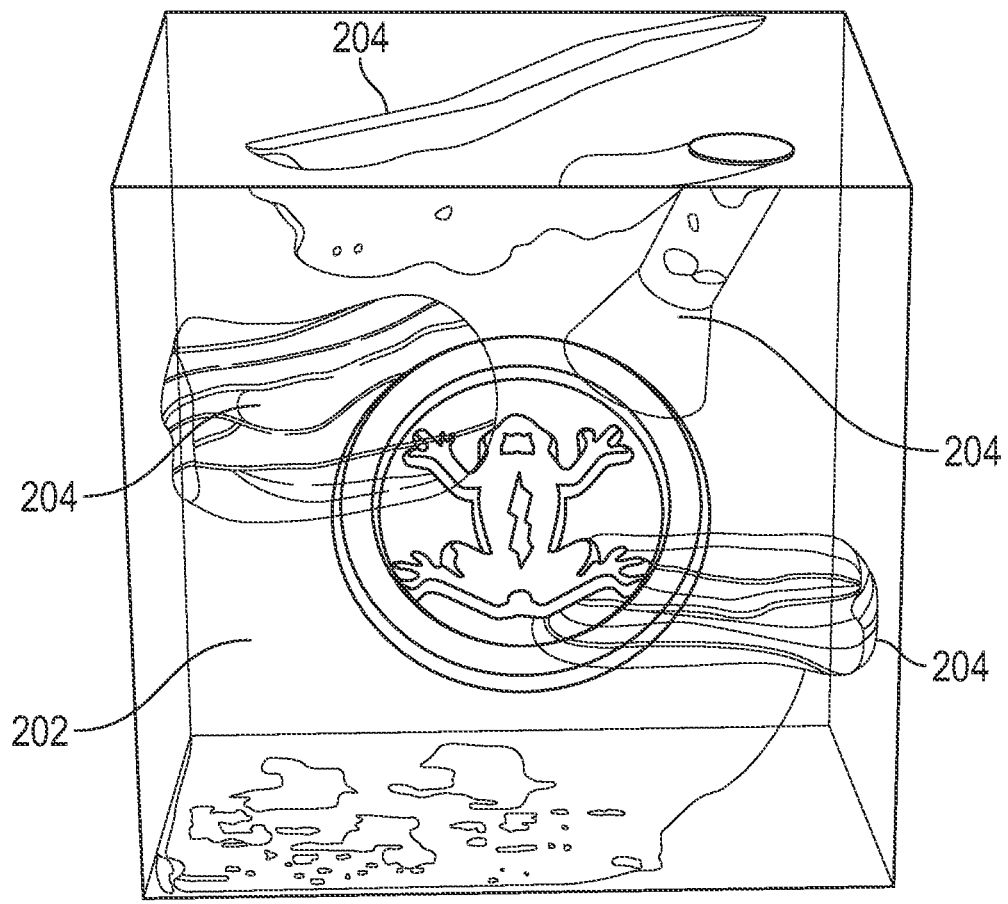
FIG. 4 depicts a diagram of an embodiment of a block from a first perspective, according to this disclosure.
Figure 5:
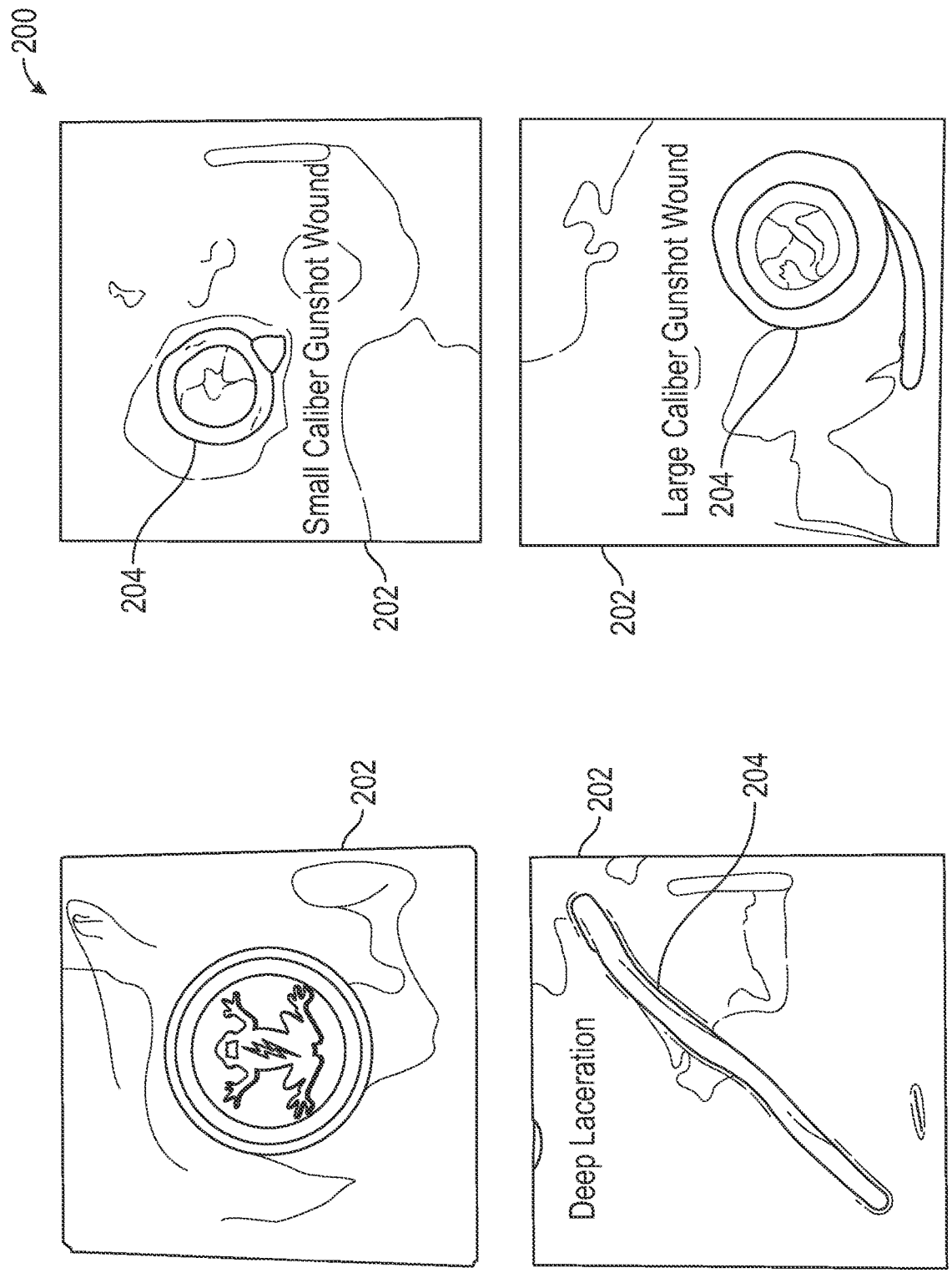
FIG. 5 depicts a diagram of an embodiment of a block from a second perspective, according to this disclosure.
Figure 6:
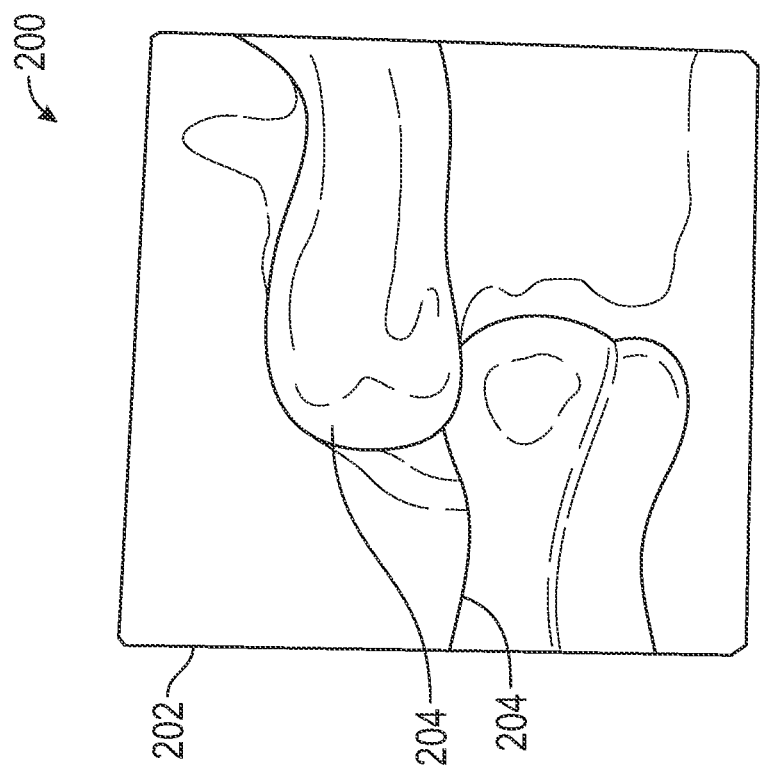
FIG. 6 depicts a diagram of an embodiment of a block from a third perspective, according to this disclosure.
Figure 6:
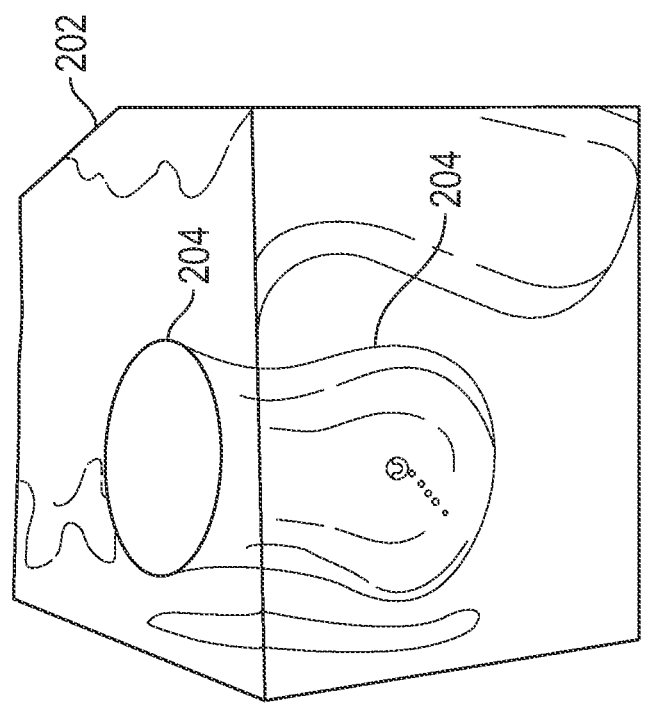

FIGS. 4-6 depict a diagram of an embodiment of a block according to this disclosure. In particular, a block 200 includes a body 202, which may be similar to the body 102, and a plurality of wells 204, which may be similar to the wells 104. In certain embodiments, the block 200, just like the block 100, is used to demonstrate a use of standard or hemostatic gauze, pressure dressings, tourniquets, or others.

Figure 7:
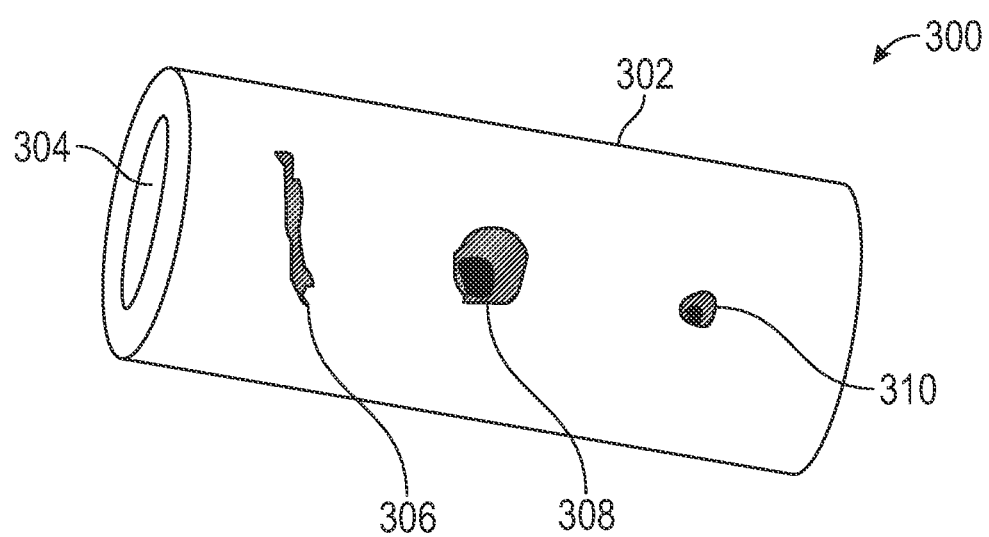
FIG. 7 depicts a diagram of an embodiment of a block with a passage, according to this disclosure.

FIG. 7 depicts a diagram of an embodiment of a wound simulator that is configured to be worn or that is slidable onto a skeletal frame (real or simulated). In particular, a block 300 includes a cylindrically shaped body 302, which may be any length so as to be positioned on an extremity of a person or skeletal frame (real or simulated). In certain embodiments, the cylindrically shaped body 302 has a length, for example, of 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, or longer than 25 cm, or any range or fraction thereof. In certain embodiments, the cylindrical shaped body 302 has a diameter of 5 cm, 6 cm, 7 cm, 8 cm, 9 cm, 10 cm, 11 cm, 12 cm, 13 cm, 14 cm, 15 cm, or greater than 15 cm, or any range or fraction thereof. In certain embodiments, the block 300 has a passage 304 running through the cylindrical shaped body 302 along the cylindrical shaped body's 302 longitudinal axis. In certain embodiments, the passage 304 has a diameter of less than 2 cm, 2 cm, 3 cm, 4 cm, 5 cm, 6 cm, 7 cm, 8 cm, 9 cm, 10 cm, or greater than 10 cm, or any range or fraction thereof.

In certain embodiments, the block 300 includes one or more wells 306, 308, 310 that are each configured to simulate a type of wound. The wells 306, 308, 310 are not in fluid communication with each other and can be identical or non-identical to each other in size, shape, volume, inner surface texture, or others. The wells 306, 308, 310 extend from the same or different sides of the cylindrical shaped body 302, although in certain embodiments a single side of the cylindrical shaped body 302 can host at least two of the wells 306, 308, 310. The wells 306, 308, 310 can be shaped in any way, such as conical, rectilinear, sinusoidal, pyramidal, wedge, tapered, ovoid, or others. The wells 306, 308, 310 include inner surfaces, which may be smooth or rough in texture. In some embodiments, at least one of the wells 306, 308, 310 is not a well but a channel extending across the cylindrical shaped body 302 end to end and in fluid communication with ambient air on both end portions. In some embodiments, two or more of the wells 306, 308, 310 are in fluid communication with each other.

Figure 8:
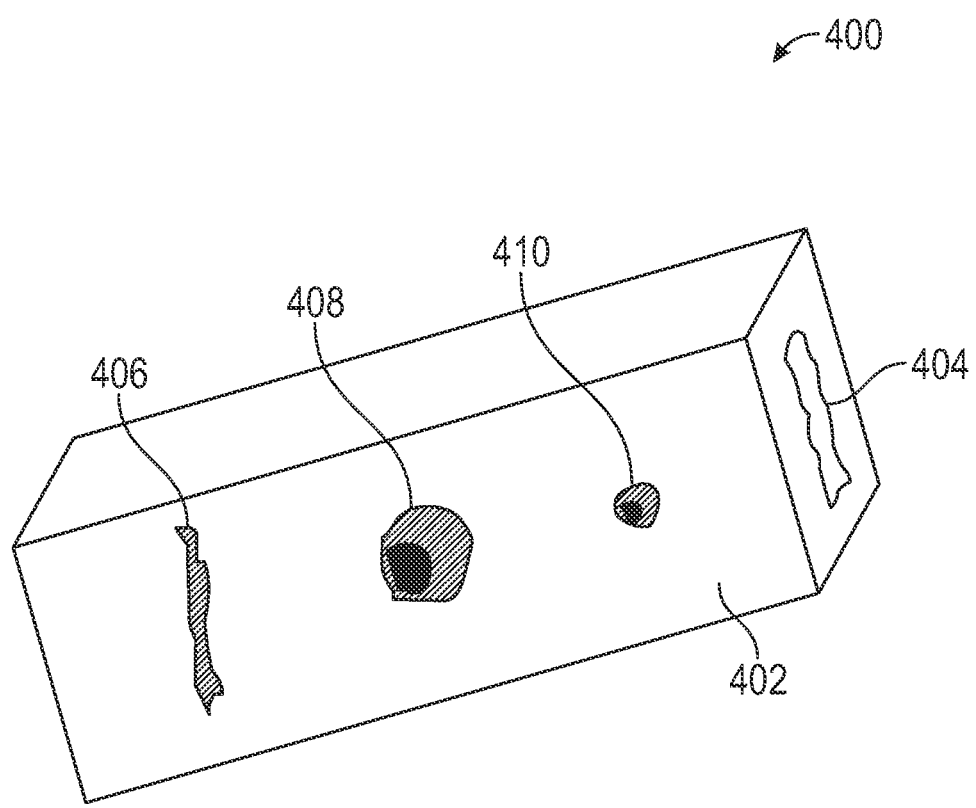
FIG. 8 depicts a diagram of an embodiment of a block with a passage, according to this disclosure.

FIG. 8 depicts a diagram of an embodiment of a wound simulator that is configured to be worn or that is slidable onto a portion of skeletal frame (real or simulated). In particular, a block 400 includes an elongated cubical shaped body 402, which may be any length so as to be positioned on an extremity of a person or a portion of a skeletal frame (real or simulated). In other embodiments, the block 400 may have different cross sections, such as, for example, triangular, pentagonal, heptagonal, hexagonal, octagonal, or any other shape. In certain embodiments, the elongated cubical shaped body 402 has a length, for example, of 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, or longer than 25 cm, or any range or fraction thereof. In certain embodiments, the elongated cubical shaped body 402 has a diameter of 5 cm, 6 cm, 7 cm, 8 cm, 9 cm, 10 cm, 11 cm, 12 cm, 13 cm, 14 cm, 15 cm, or greater than 15 cm, or any range or fraction thereof. In certain embodiments, the block 400 has a passage 404 running through the elongated cubical shaped body 402 along the elongated cubical shaped body's 402 longitudinal axis. In certain embodiments, the passage 404 has a diameter of less than 2 cm, 2 cm, 3 cm, 4 cm, 5 cm, 6 cm, 7 cm, 8 cm, 9 cm, 10 cm, or greater than 10 cm, or any range or fraction thereof.

In certain embodiments, the block 400 includes one or more weds 406, 408, 410 that are each configured to simulate a type of wound. The wells 406, 408, 410 are not in fluid communication with each other and can be identical or non-identical to each other in size, shape, volume, inner surface texture, or others. The wells 406, 408, 410 extend from the same or different sides of the elongated cubical shaped body 402, although in certain embodiments a single side of the elongated cubical shaped body 402 can host at least two of the wells 406, 408, 410. The wells 406, 408, 410 can be shaped in any way, such as conical, rectilinear, sinusoidal, pyramidal, wedge, tapered, ovoid, or others. The wells 406, 408, 410 include inner surfaces, which may be smooth or rough in texture. In some embodiments, at least one of the wells 406, 408, 410 is not a well but a channel extending across the elongated cubical shaped body 402 end to end and in fluid communication with ambient air on both end portions. In some embodiments, two or more of the wells 406, 408, 410 are in fluid communication with each other.

Figure 9:
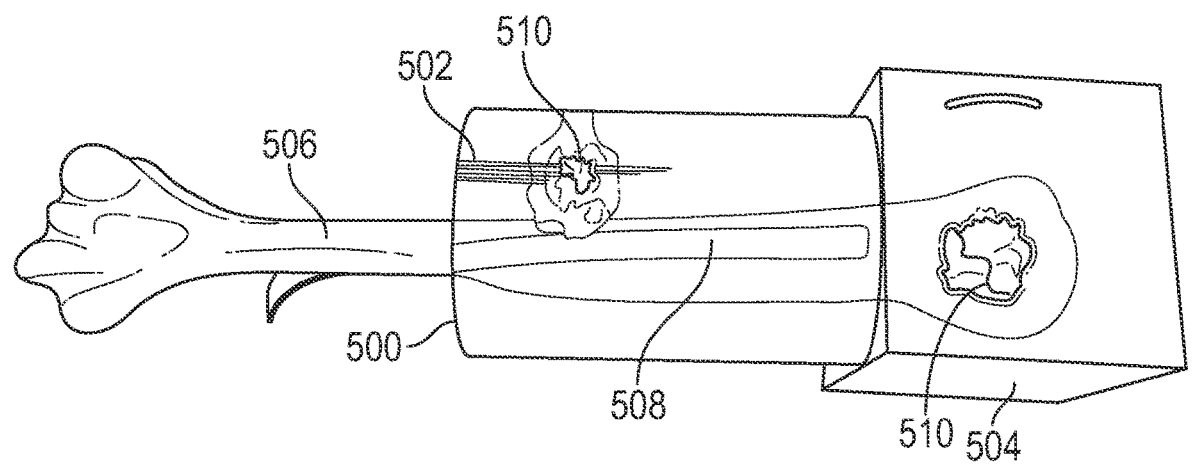
FIG. 9 depicts a diagram of an embodiment of a block including a bone and hollow tube, according to this disclosure.
Figure 10:
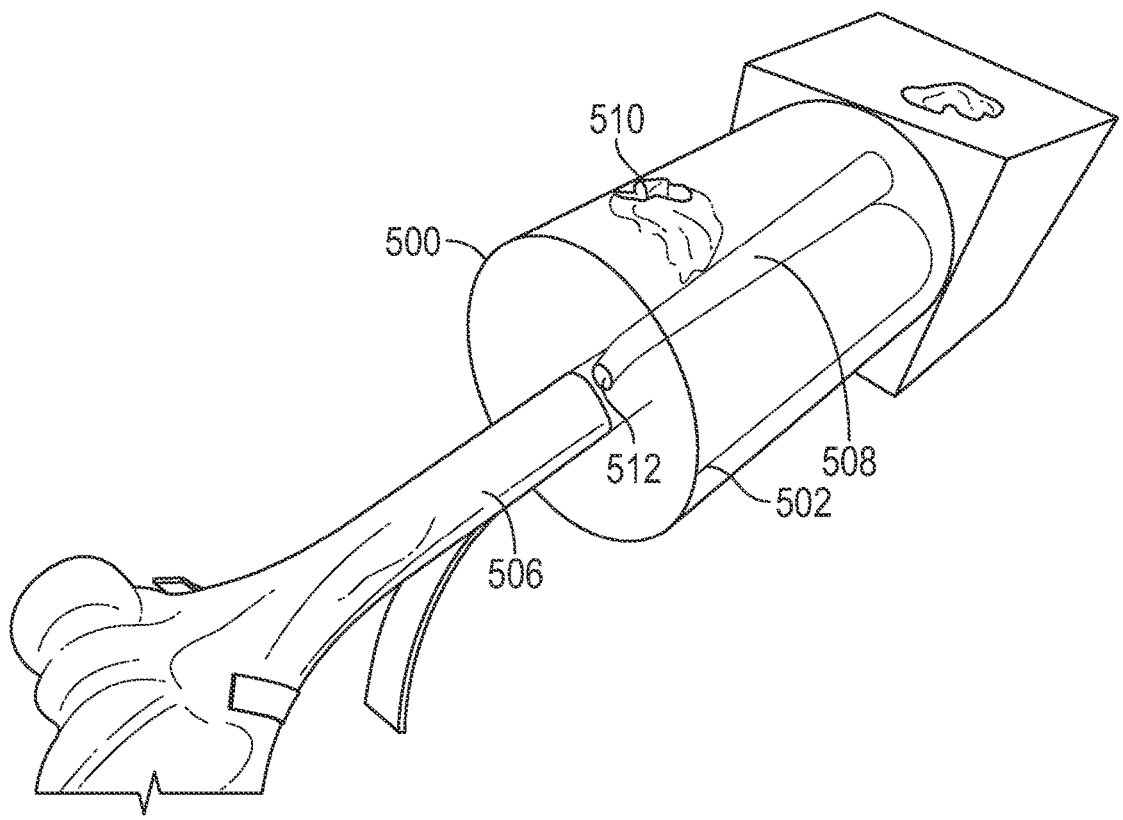
FIG. 10 depicts a diagram of an embodiment of a block including a bone and hollow tube, according to this disclosure.
Figure 11:
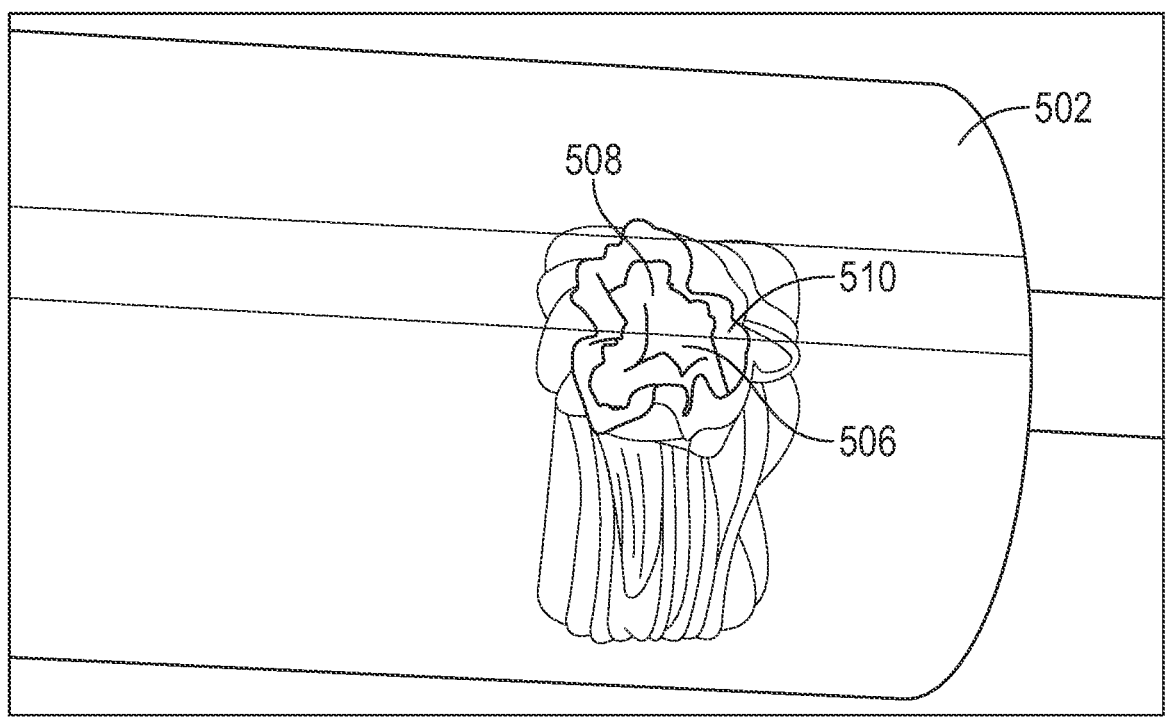
FIG. 11 depicts a diagram of an embodiment of a block including a bone and hollow tube, according to this disclosure.
Figure 12:
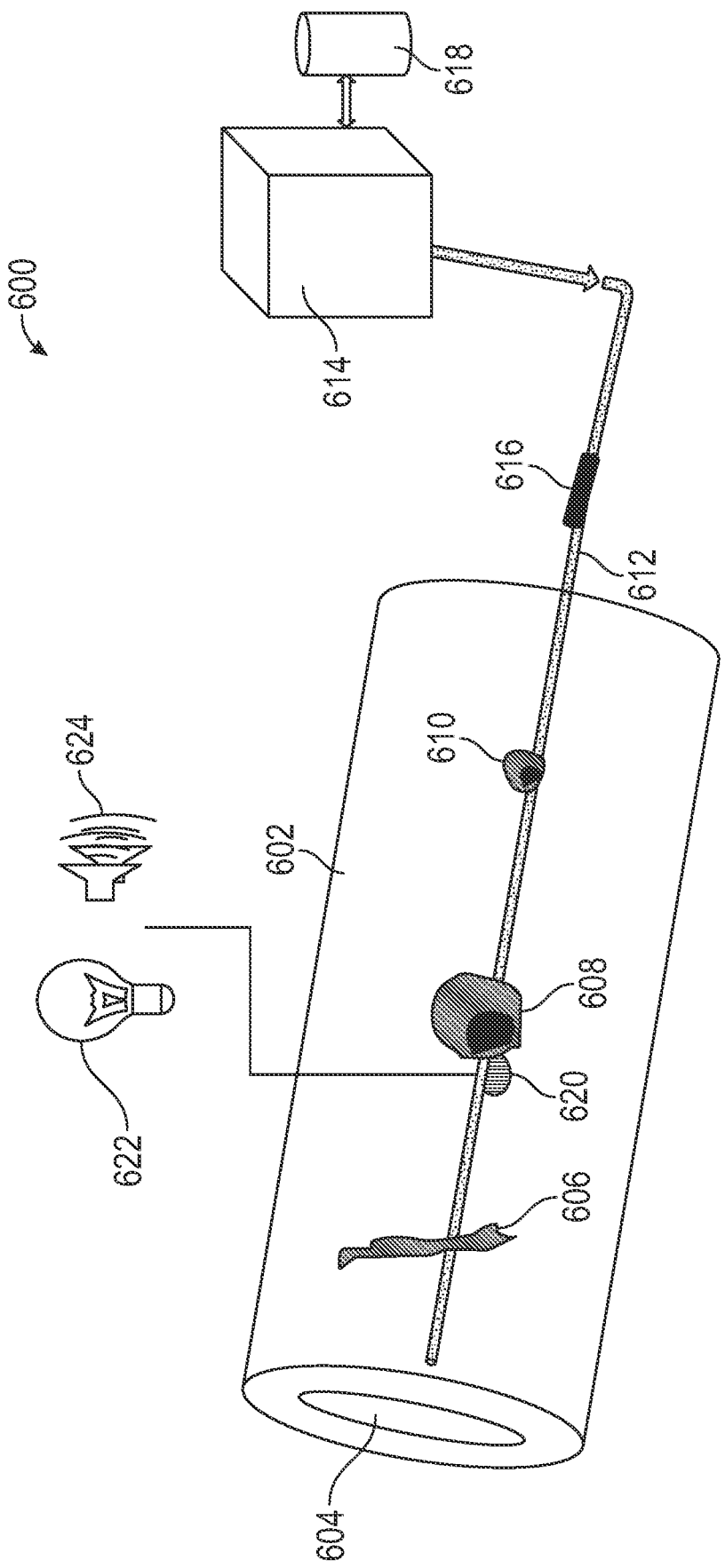
FIG. 12 depicts a diagram of an embodiment of a block, according to this disclosure.

In certain embodiments, for example, as shown in FIGS. 9, 10 and 11, a block 500 is formed as a cylindrical shaped body 502 and a cubical shaped body 504 around a skeletal structure, for example, a bone 506. The bone 506 is positioned, inserted or embedded within the block 500, such that the block 500 and the bone 506 form a unitary structure. The block also includes a well 510, that simulates an injury, such as, for example, a gunshot wound, a stab wound, a puncture, or some other injury. In certain embodiments, for example, as shown in FIGS. 9 and 10, positioned along the bone 506 is a hollow tube 508 that is a simulator of a vessel of a bodily fluid, such as, for example, a vein or artery, for purposes of enhanced training using the block 500. As shown in FIG. 12, in the enhanced training, the hollow tube 612 is coupled to a pump 614 via a connector 616, which is configured to pump a liquid through the hollow tube 612. In certain embodiments, for example, the hollow tube 612 includes at least one of plastic, metal, rubber, wood, or other materials. Note that the hollow tube 612 is visible within the cylindrical shaped body 602. As such, the simulator is visually distinct from the cylindrical shaped body 602, such as via contrast, color, or others. In some embodiments, the hollow tube 612 is not visible or only partially visible within the cylindrical shaped body 602. In certain embodiments, the hollow tube 612 represents any vessel within a mammal, such as a human or others. In certain embodiments, for example, the vessel includes an artery, a vein, a trachea, a windpipe, or others. Note that in certain embodiments, the vessel includes an intersection of vessels. In certain embodiments, the bodily fluid includes simulated blood, saliva, urine, or others. As such, in certain embodiments, the fluid is simulated based on color, consistency, texture, or others. For example, in certain embodiments, the fluid is red in color to simulate blood or thick to simulate mucus. Therefore, in certain embodiments, the fluid is output via the simulator from the cylindrical shaped body 602. In some embodiments, a source of the fluid is contained within the cylindrical shaped body 602 or external to the cylindrical shaped body 602. In certain embodiments, the source of the fluid includes a reservoir 618 and a pump 614, with the reservoir 618 containing the fluid and the pump 614 pumping the fluid. In some embodiments, at least one of the cylindrical shaped body 602 or the well 606, 608, 610 includes a pressure sensor 620, whether analog or digital, configured to sense if the user is applying appropriate wound pressure and outputs a signal based on the sensing, such as to a bulb 622 or a speaker 624, if the appropriate wound pressure passes or fails to pass a predefined threshold. In some embodiments, the signal from the pressure sensor 620 is used to control the pump 614, such as, for example, activating or deactivating the pump 614. In some embodiments, as shown in FIG. 11, the well 510 is configured to receive a gauze strip. Therefore, the gauze strip can be manually inserted into the well 510 to stop the simulator of the vessel of the bodily fluid from outputting the bodily fluid, such as to educate on how to stop or stem bleeding or others.

In one of operation, during a training class, through the block 100, 200, 300, 400, 500, 600, an instructor can insert a gauze strip into at least one of the wells 104, 204, 306, 308, 310, 406, 408, 410, 510, 606, 608, 610 and see from a side whether the gauze strip inserted are deep enough. For example, the block 100, 200, 300, 400, 500, 600 can be used as a platform for learning hemorrhage control/wound packing techniques used in an effective application of a gauze product. This helps trainees develop required muscle memory as well as an understanding of various mechanical aspects of wound packing, while providing for a suitable and realistic tactile sensation.

Features described with respect to certain example embodiments can be combined and sub-combined in and/or with various other example embodiments. Also, different aspects and/or elements of example embodiments, as disclosed herein, can be combined and sub-combined in a similar manner as well. Further, some example embodiments, whether individually and/or collectively, can be components of a larger system, wherein other procedures can take precedence over and/or otherwise modify their application. Additionally, a number of steps can be required before, after, and/or concurrently with example embodiments, as disclosed herein. Note that any and/or all methods and/or processes, at least as disclosed herein, can be at least partially performed via at least one entity in any manner.

Example embodiments of this disclosure are described herein with reference to illustrations of idealized embodiments (and intermediate structures) of this disclosure. As such, variations from various illustrated shapes as a result, for example, of manufacturing techniques and/or tolerances, are to be expected. Thus, various example embodiments of this disclosure should not be construed as necessarily limited to various particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing, and/or other any other types of manufacturing. For example, some manufacturing processes include three dimensional (3D) printing, laser cutting, computer numerical control routing, milling, pressing, stamping, vacuum forming, hydroforming, injection molding, lithography, and so forth.

Any and/or all elements, as disclosed herein, can be and/or include, whether partially and/or fully, a solid, including a metal, a mineral, an amorphous material, a ceramic, a glass ceramic, an organic solid, such as wood and/or a polymer, such as rubber, a composite material, a semiconductor, a nanomaterial, a biomaterial and/or any combinations thereof. Any and/or all elements, as disclosed herein, can be and/or include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, opaqueness, luminescence, reflection, phosphorescence, anti-reflection and/or holography, a photo-sensitive coating, an electronic and/or thermal property coating, such as for passivity, insulation, resistance or conduction, a magnetic coating, a water-resistant and/or waterproof coating, a scent coating and/or any combinations thereof. Any and/or all elements, as disclosed herein, can be rigid, flexible, and/or any other combinations thereof. Any and/or all elements, as disclosed herein, can be identical and/or different from each other in material, shape, size, color and/or any measurable dimension, such as length, width, height, depth, area, orientation, perimeter, volume, breadth, density, temperature, resistance, and so forth.

Unless otherwise defined, all terms (including technical and scientific terms) used herein have the same meaning as commonly understood by one of ordinary skill in an art to which this disclosure belongs. Various terms, such as those defined in commonly used dictionaries, should be interpreted as having a meaning that is consistent with a meaning in a context of a relevant art and should not be interpreted in an idealized and/or overly formal sense unless expressly so defined herein.

Furthermore, relative terms such as "below," "lower," "above," and "upper" can be used herein to describe one element's relationship to another element as illustrated in the set of accompanying illustrative drawings. Such relative terms are intended to encompass different orientations of illustrated technologies in addition to an orientation depicted in the set of accompanying illustrative drawings. For example, if a device in the set of accompanying illustrative drawings were turned over, then various elements described as being on a "lower" side of other elements would then be oriented on "upper" sides of other elements. Similarly, if a device in one of illustrative figures were turned over, then various elements described as "below" or "beneath" other elements would then be oriented "above" other elements. Therefore, various example terms "below" and "lower" can encompass both an orientation of above and below.

As used herein, a term "about" and/or "substantially" refers to a +/−10% variation from a nominal value/term. Such variation is always included in any given value/term provided herein, whether or not such variation is specifically referred thereto.

If any disclosures are incorporated herein by reference and such disclosures conflict in part and/or in whole with this disclosure, then to an extent of a conflict, if any, and/or a broader disclosure, and/or broader definition of terms, this disclosure controls. If such disclosures conflict in part and/or in whole with one another, then to an extent of a conflict, if any, a later-dated disclosure controls.

In some embodiments, various functions or acts can take place at a given location and/or in connection with the operation of one or more apparatuses or systems. In some embodiments, a portion of a given function or act can be performed at a first device or location, and a remainder of the function or act can be performed at one or more additional devices or locations.

The corresponding structures, materials, acts, and equivalents of all means or step plus function elements in the claims below are intended to include any structure, material, or act for performing the function in combination with other claimed elements as specifically claimed. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the steps can be performed in a differing order or steps can be added, deleted or modified. All of these variations are considered a part of the disclosure. It will be understood that those skilled in the art, both now and in the future, can make various improvements and enhancements which fall within the scope of the claims which follow.

The description of this disclosure has been presented for purposes of illustration and description, but is not intended to be fully exhaustive and/or limited to the disclosure in the form disclosed. Many modifications and variations in techniques and structures will be apparent to those of ordinary skill in an art without departing from a scope and spirit of this disclosure as set forth in the claims that follow. Accordingly, such modifications and variations are contemplated as being a part of this disclosure. A scope of this disclosure is defined by various claims, which include known equivalents and unforeseeable equivalents at a time of filing of this disclosure.

The invention claimed is:

1. A method comprising:
    accessing a block comprising an elastic material that is not opaque, a plurality of sides, a plurality of wells, a first well and a second well, wherein the first well is positioned on a first side of the block and the second well is positioned on a second side of the block, wherein none of the plurality of wells is in fluid communication with another of the plurality of wells;
    directing a user on a proper technique for practicing packing a wound by placing gauze into at least one of the plurality of wells; and
    notifying a user of successful packing of at least one of the first well or the second well via at least one of a light, a sound, or a signal through a speaker activated by a sensor positioned within the block.

2. The method of claim 1, wherein the wells are different from each other in shape.

3. The method of claim 1, wherein the wells are different from each other in volume.

4. The method of claim 1, wherein the block is transparent.

5. The method of claim 1, wherein the block is translucent.

6. The method of claim 1, wherein the block includes a side from which the wells extend.

7. The method of claim 1, wherein the block includes a plurality of sides from which the wells extend, wherein the sides correspond to the wells in a one-to-one manner.

8. The method of claim 1, wherein the block is polygonal.

9. The method of claim 1, wherein the block is at least one of a sphere, an ovoid, an ellipsoid, or cylindrical.

10. The method of claim 1, wherein at least one of the wells includes an inner surface that is smooth.

11. The method of claim 1, wherein at least one of the wells includes an inner surface that is rough.

12. The method of claim 1, wherein the elastic material includes at least one of a gelatin or a silicon.

13. The method of claim 1, wherein the block contains a simulator of a bone.

14. The method of claim 1, wherein the block contains a simulator of a vessel of a bodily fluid.

15. The method of claim 1, further comprising:
    inserting a gauze strip into at least one of the wells.

16. The method of claim 1, further comprising:
    outputting a fluid from the block.

17. The method of claim 16, wherein the fluid simulates a blood.

18. The method of claim 1, wherein the block includes a pressure sensor positioned within the block and configured to output a signal based on a force applied thereto.

19. The method of claim 18, wherein the pressure sensor is internal to at least one of the wells.

20. The method of claim 1, wherein the opacity of the block changes based on application of at least one of a chemical, an electrical signal, or a light source.

21. The method of claim 1, further comprising providing a storage medium storing a set of instructions on how to use the block to learn how to pack a wound.

22. A device comprising:
a block comprising an elastic material, a plurality of sides, a first well and a second well, wherein the block is not opaque, wherein the first well is positioned on a first side of the block and the second well is positioned on a second side of the block, wherein the first well is not in fluid communication with the second well, wherein the first well comprises a simulator of a first wound, and the second well comprises a simulator of a second type of wound.

23. The device of claim 22, wherein the wells are different from each other in shape.

24. The device of claim 22, wherein the wells are different from each other in volume.

25. The device of claim 22, wherein the block is transparent.

26. The device of claim 22, wherein the block is translucent.

27. The device of claim 22, wherein the block includes a side from which the wells extend.

28. The device of claim 22, wherein the block includes a plurality of sides from which the wells extend, wherein the sides correspond to the wells in a one-to-one manner.

29. The device of claim 22, wherein the block is polygonal.

30. The device of claim 22, wherein the block is at least one of a sphere, an ovoid, an ellipsoid, or cylindrical.

31. The device of claim 22, wherein at least one of the wells includes an inner surface that is smooth.

32. The device of claim 22, wherein at least one of the wells includes an inner surface that is rough.

33. The device of claim 22, wherein the elastic material includes at least one of a gelatin or a silicon.

34. The device of claim 22, wherein the block contains a simulator of a bone.

35. The device of claim 22, wherein the block contains a simulator of a vessel of a bodily fluid.

36. The device of claim 22, further comprising:
a gauze strip positioned in at least one of the wells.

37. The device of claim 22, further comprising:
a fluid, wherein the fluid is emitted from the block.

38. The device of claim 37, wherein the fluid simulates a blood.

39. The device of claim 22, wherein the block includes a pressure sensor positioned within the block and configured to output a signal based on a force applied thereto.

40. The device of claim 39, wherein the pressure sensor is internal to at least one of the wells.

41. The device of claim 22, wherein the opacity of the block changes based on upon application of at least one of a chemical, an electrical signal, or a light source.

42. The device of claim 22, further comprising a simulator of at least one of a bone or a vessel of a bodily fluid.

* * * * *